(12) United States Patent
Miwa

(10) Patent No.: US 6,537,215 B2
(45) Date of Patent: Mar. 25, 2003

(54) NON-CONTACT TYPE TONOMETER

(75) Inventor: Tetsuyuki Miwa, Nukata-gun (JP)

(73) Assignee: Nidek, Co., Ltd., Gamagori (JP)

( * ) Notice: Subject to any disclaimer, the term of this patent is extended or adjusted under 35 U.S.C. 154(b) by 62 days.

(21) Appl. No.: 09/907,770

(22) Filed: Jul. 19, 2001

(65) Prior Publication Data

US 2002/0049373 A1 Apr. 25, 2002

(30) Foreign Application Priority Data

Jul. 26, 2000 (JP) ........................................ 2000-231361

(51) Int. Cl.$^7$ ................................................. A61B 3/16
(52) U.S. Cl. ........................ 600/405; 351/205; 351/221
(58) Field of Search ................................ 351/205, 221; 600/398, 399, 401, 405, 558

(56) References Cited

U.S. PATENT DOCUMENTS

| | | | |
|---|---|---|---|
| 4,951,670 A | 8/1990 | Tanaka et al. | 600/401 |
| 5,033,841 A * | 7/1991 | Nishio et al. | 600/398 |
| 5,107,851 A * | 4/1992 | Yano et al. | 600/405 |
| 5,165,409 A * | 11/1992 | Coan | 600/405 |
| 5,279,300 A | 1/1994 | Miwa et al. | 128/648 |
| 5,502,521 A | 3/1996 | Katou | 351/221 |
| 5,946,073 A | 8/1999 | Miwa | 351/205 |
| 5,947,898 A * | 9/1999 | Suzuki et al. | 600/405 |
| 6,042,544 A | 3/2000 | Miwa et al. | 600/399 |
| 6,159,148 A * | 12/2000 | Luce | 600/405 |
| 6,234,966 B1 | 5/2001 | Miwa | 600/401 |

FOREIGN PATENT DOCUMENTS

| | | |
|---|---|---|
| JP | A 5-42109 | 2/1993 |
| JP | A 9-215662 | 8/1997 |

* cited by examiner

*Primary Examiner*—Marvin M. Lateef
*Assistant Examiner*—John R. Sanders
(74) *Attorney, Agent, or Firm*—Oliff & Berridge, PLC

(57) ABSTRACT

A non-contact type tonometer includes a compressed air blowing unit which compresses air in a cylinder by means of a piston disposed within the cylinder and blows the compressed air to a cornea of an examinee's eye; a driving unit which drives the piston; a pressure sensor which detects pressure of the air in the cylinder; an optical system which projects light to the cornea; a photosensor which detects, of the light projected by the optical system, reflection light reflected from the cornea; and a controller which obtains a change in pressure for a predetermined time based on a detection result by the pressure sensor when the photosensor detects a predetermined change amount of the reflection light after the driving unit drives the piston to start blowing of the compressed air to the cornea from the compressed air blowing unit, and changes a timing of stopping supply of driving power to the driving unit based on the obtained change in pressure.

12 Claims, 4 Drawing Sheets

NON-CONTACT TYPE TONOMETER

BACKGROUND OF THE INVENTION

1. Field of the Invention

The present invention relates to a non-contact type tonometer for measuring intraocular pressure of an examinee's eye by detecting a deformed state of a cornea of the eye caused by a blow of a compressed air (fluid) thereto.

2. Description of Related Art

There has conventionally been known a non-contact type tonometer used for measuring the intraocular pressure of an eye of an examinee by detecting a deformed state of a cornea of the eye caused by an air blow from an air blowing device. A corneal deformation detecting system of this tonometer is constructed of a projection optical system for projecting light to the cornea and a detecting optical system including a photodetector (photosensor) for detecting the amount of light reflected from the cornea. By detecting that the amount of the corneal reflection light detected by the photodetector became the maximum, a deformed state of the cornea is detected.

In the conventional tonometer, however, even when driving of the air blowing device is stopped after detection that the cornea has been deformed into a predetermined state, the air blow is not stopped immediately, thus allowing superfluous air to be blown to the eye. If the examinee blinks his/her eye to be examined, the amount of the corneal reflection light detected by the photodetector of the corneal deformation detecting system does not produce any peak. As a result, the air would be blown at the predetermined maximum pressure against the examinee's eye. This results in a burden to the examinee's eye.

SUMMARY OF THE INVENTION

The present invention has been made in view of the above circumstances and has an object to overcome the above problems and to provide a non-contact type tonometer capable of reducing a burden to an examinee's eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided A non-contact type tonometer including: a compressed air blowing unit which compresses air in a cylinder by means of a piston disposed within the cylinder and blows the compressed air to a cornea of an examinee's eye; a driving unit which drives the piston; a pressure sensor which detects pressure of the air in the cylinder; an optical system which projects light to the cornea; a photosensor which detects, of the light projected by the optical system, reflection light reflected from the cornea; and a controller which obtains a change in pressure for a predetermined time based on a detection result by the pressure sensor when the photosensor detects a predetermined change amount of the reflection light after the driving unit drives the piston to start blowing of the compressed air to the cornea from the compressed air blowing unit, and changes a timing of stopping supply of driving power to the driving unit based on the obtained change in pressure.

According to another aspect of the present invention, there is provided a non-contact type tonometer including: a compressed air blowing unit which compresses air in a cylinder by means of a piston disposed within the cylinder and blows the compressed air to a cornea of an examinee's eye; a driving unit which drives the piston; a pressure sensor which detects pressure of the air in the cylinder; an optical system which projects light to the cornea; a one-dimensional position detecting element which detects reflection light corresponding to a working distance to the cornea based on the light projected by the optical system and then reflected from the cornea; and a controller which obtains a change in pressure for a predetermined time based on a detection result by the pressure sensor when the one-dimensional position detecting element detects a predetermined change amount of the reflection light after the driving unit drives the piston to start blowing of the compressed air to the cornea from the compressed air blowing unit, and changes a timing of stopping supply of driving power to the driving unit based on the obtained change in pressure.

According to the third aspect of the present invention, there is provided a non-contact type tonometer including: a compressed air blowing unit which compresses air in a cylinder by means of a piston disposed within the cylinder and blows the compressed air to a cornea of an examinee's eye; a driving unit which drives the piston; a pressure sensor which detects pressure of the air in the cylinder; an optical system which projects light to the cornea; a photosensor which detects, of the light projected by the optical system, reflection light reflected from the cornea; and a controller which obtains a pressure change ratio expressed in a pressure change amount with respect to a predetermined time just before a predetermined change amount of the reflection light is detected by the photosensor after the driving unit drives the piston to start blowing of the compressed air to the cornea from the compressed air blowing unit, and sets the pressure change amount to a small value when the obtained pressure change ratio is large and, alternatively, to a large value when the obtained pressure change ratio is small, and stops supply of driving power to the driving unit based on the set pressure change amount.

According to the fourth aspect of the present invention, there is provided a non-contact type tonometer including: a compressed air blowing unit which compresses air in a cylinder by means of a piston disposed within the cylinder and blows the compressed air to a cornea of an examinee's eye; a driving unit which drives the piston; an optical system which projects light to the cornea; a photosensor which detects, of the light projected by the optical system, reflection light reflected from the cornea; and a controller which judges that a blink of the examinee's eye has occurred when a change amount of the reflection light detected by the photosensor decreases by a predetermined amount after the driving unit drives the piston to start blowing of the compressed air to the cornea from the compressed air blowing unit, and stops supply of driving power to the driving unit.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
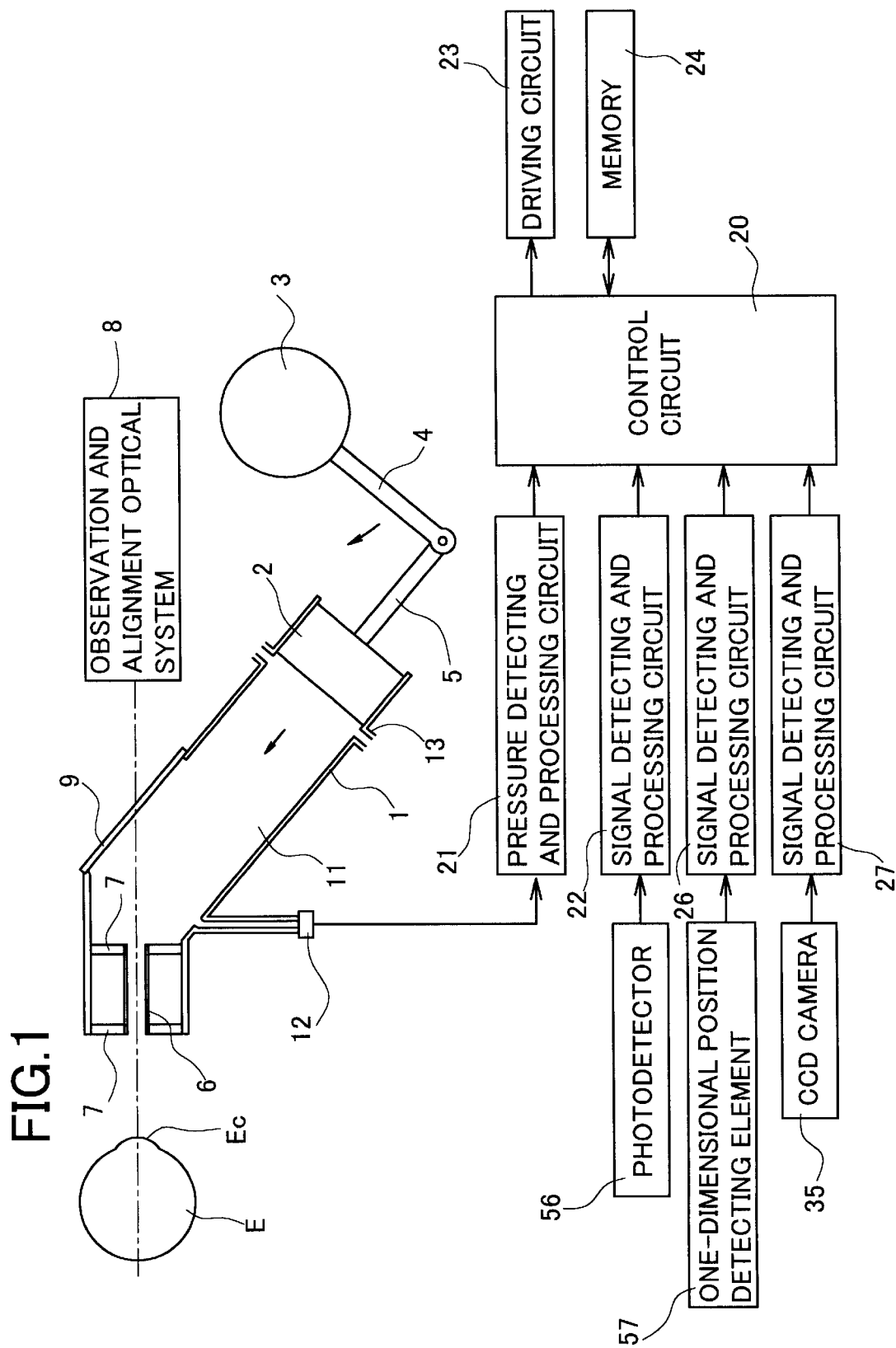
FIG. 1 is a schematic side view of an air blowing mechanism and a block diagram of main parts of a control system of a non-contact type tonometer in an embodiment according to the present invention.

A detailed description of a preferred embodiment of a non-contact type tonometer embodying the present invention will now be given referring to the accompanying drawings. FIG. 1 is a schematic side view of an air blowing mechanism and a block diagram of main parts of a control system of the non-contact type tonometer in the present embodiment.

Numeral 1 is a cylinder portion for air compression, which is provided in an inclined position to the horizontal line of the tonometer body; 2, a piston; and 3, a rotary solenoid. When electric charge (current or voltage) is supplied as driving energy (power) to the solenoid 3, the piston 2 is pushed up within the cylinder portion 1 through an arm 4 and a connecting rod (piston rod) 5. Numeral 11 is an air compression chamber. The air, which has been compressed by the rise of the piston 2 in the compression chamber 11, is blown from a nozzle 6 toward the cornea Ec of an examinee's eye E. The rotary solenoid 3 is provided with a coiled spring (not shown). When the supply of the electric charge is cut off, the piston 2 is caused to lower to the initial position by the biasing force of the coiled spring in the lowering direction.

Numeral 7 is a transparent glass plate, which holds the nozzle 6 and transmits observation light and alignment light. The glass plate 7 also constitutes a side wall of the air compression chamber 11. Numeral 9 is a transparent glass plate that is provided behind the nozzle 6 and constitutes the rear wall of the air compression chamber 11, transmitting observation light and alignment light. Arranged behind the glass plate 9 is an optical system 8 for observation and alignment which will be mentioned later.

Numeral 12 is a pressure sensor for detecting the pressure in the compression chamber 11. Numeral 13 is an air vent hole, which is used to reduce the resistance until the initial speed is given to the piston 2 and to provide a pressure change proportional to time at pressure rise time.

Numeral 20 is a control circuit, connected to a pressure detecting and processing circuit 21 for signals from the sensor 12, a signal detecting and processing circuit 22 for signals from a photodetector (photosensor) 56, a signal detecting and processing circuit 26 for signals from a one-dimensional position detecting element 57, a signal detecting and processing circuit 27 for signals from a CCD camera 35, a driving circuit 23 for driving the rotary solenoid 3, and a memory 24 for storing measurement data and others.

Figure 2:
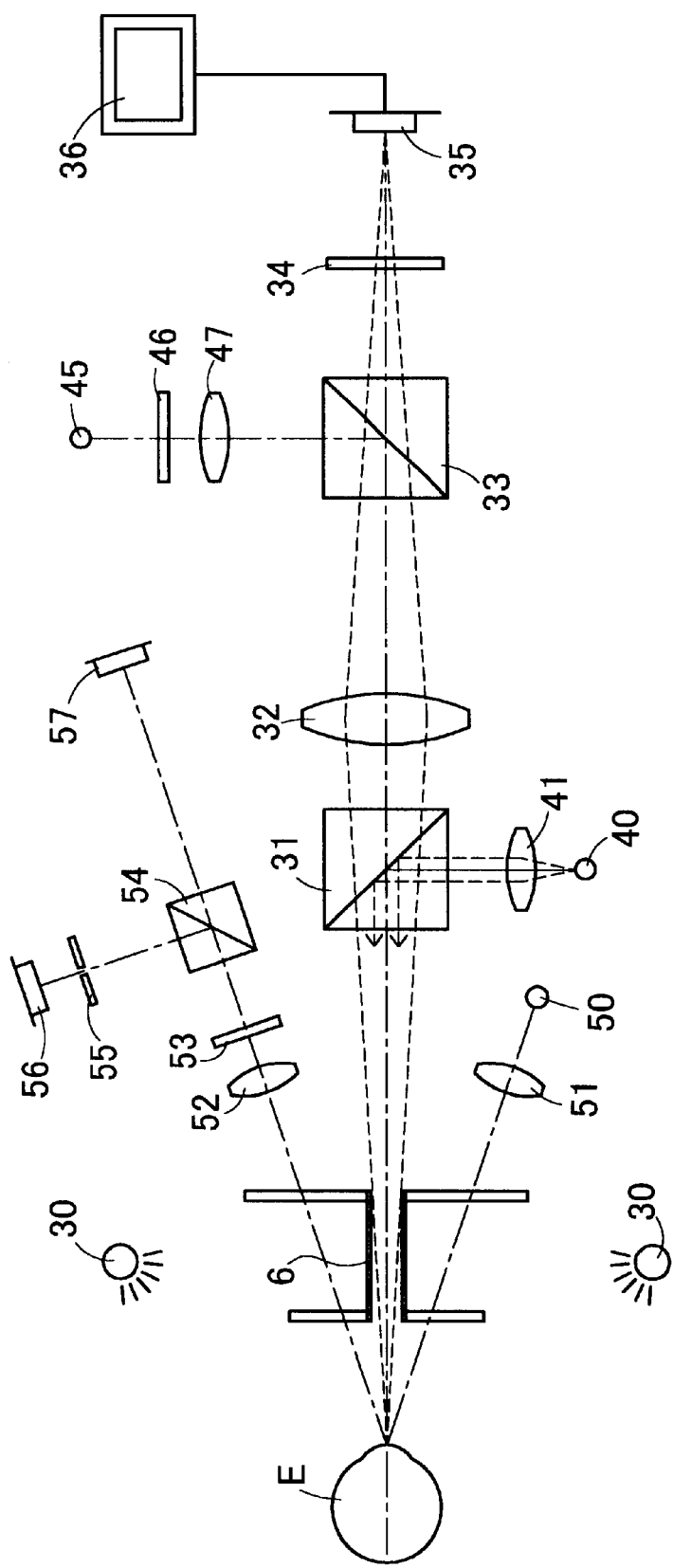
FIG. 2 is a schematic view of an optical system seen from above, provided near a nozzle in the air blowing mechanism.

FIG. 2 is a schematic view of the optical system 8 seen from above, arranged near the nozzle 6 of the air blowing mechanism.

Numeral 30 is each of infrared light sources for observation. When the examinee's eye E is illuminated by the infrared light emitted from the light sources 30, the image of the eye E is formed on the CCD camera 35 through a beam splitter 31, an objective lens 32, a beam splitter 33, and a filter 34. This filter 34 has the property of passing the light of the light source 30 and the light of a light source 40, while not passing the light of a light source 50. The image thus formed on the CCD camera 35 is displayed on a monitor 36.

Numeral 40 is a light source (infrared LED) for alignment. The light emitted from the light source 40, allowed to pass through a projection lens 41, is reflected by the beam splitter 31 and is projected to the cornea Ec from the front. This light from the light source 40 forms a luminescent spot (an index image) on or near the corneal apex (vertex), which then forms an image on the CCD camera 35 through the components; the beam splitter 31, the objective lens 32, the beam splitter 33, and the filter 34. This index image is used for alignment in up-and-down and right-and-left directions with respect to the examinee's eye E.

Numeral 45 is a light source (visible LED) used for projecting a fixation mark or target. The light in the form of a fixation mark 46 illuminated by the light source 45 passes through a projection lens 47 and is reflected by the beam splitter 33 toward the eye E. Measurement is performed while the examinee fixes his/her eye E on the fixation mark 46.

Numeral 50 is a light source (infrared LED) used for detecting corneal deformation. The light emitted from the light source 50 is made into substantial parallel luminous flux by a collimator lens 51, and is projected to the cornea Ec. The light reflected from the cornea Ec passes through a light-receiving lens 52 and a filter 53 having the property of not passing the light of the light sources 30 and 40, and then is reflected by a beam splitter 54. The thus reflected light passes through a pin-hole plate 55 and is detected (received) by a photodetector 56. The optical system for corneal deformation detection is arranged so that the amount of light received by the photodetector 56 becomes the maximum when the cornea Ec is deformed into a predetermined state (an applanation state).

In the present embodiment, a part of the above corneal deformation detecting optical system is used in common for an optical system for detecting a working distance. The light emitted from the light source 50 forms a virtual image of the light source 50 as an index image. The light of the index image passes through the lens 52, the filter 53, the beam splitter 54 and is made incident on the one-dimensional position detecting element 57 such as a position sensing device (PSD), a line sensor, or the like. As the eye E (the cornea Ec) moves in the working distance direction, the incident position of the index image of the light source 50 similarly shifts on the detecting element 57. The control circuit 20 therefore can obtain information on the working distance based on output signals from the detecting element 57. The control circuit 20 can also detect the deformation state of the cornea Ec and whether or not an eye blink occurs based on the output signals from the detecting element 57 (which will be mentioned later). Based on the information, the control circuit 20 controls the driving of the solenoid 3. It is to be noted that the corneal deformation detecting optical system and the working distance detecting optical system may be configured separately.

The operation of the non-contact type tonometer constructed as above will be described hereinafter. At first, explanation is made on the case where no blink of the eye E occurs after the start of measurement.

The examiner instructs the examinee to fix his/her eye E in place and operates a joystick not shown based on the alignment information displayed on the monitor 36 to adjust alignment of the apparatus. The alignment in up-and-down and right-and-left directions is performed so that a reticle (not shown) displayed on the monitor 36 and the index image formed by the light source 40 are brought in a predetermined positional relation. The alignment in the working distance direction is performed so that a distance mark displayed based on the working distance information obtained from the detecting element 57 is brought into a predetermined state. It is to be noted that the details of the alignment adjustment are referred to U.S. Pat. No. 5,502,521 (Japanese Patent Unexamined Publication No. 7-23907) filed by the same applicant as that of the present invention. Alternatively, the alignment may automatically be effected by moving a measuring section on the basis of the detection information on each of the index images.

Upon detection of completion of the alignment, the control circuit 20 automatically generates a trigger signal to start measurement. Alternatively, the examiner may input a trigger signal with a measurement start switch or the like. The measurement is thus started. To be more specific, the control circuit 20 causes the driving circuit 23 to supply electric charge to the rotary solenoid 3 as driving energy making the rotary solenoid 3 operable, thus activating the rotary solenoid 3.

The supply of electric charge to the rotary solenoid 3 causes the rise of the piston 2, compressing the air in the compression chamber 11. The compressed air is blown from the nozzle 6 toward the cornea Ec. The cornea Ec is gradually deformed by the compressed air thus blown. Of the light projected by the LED 50, the reflection light from the cornea Ec is detected by the photodetector 56. Based on the output signal from the photodetector 56, the deformed state of the cornea Ec is detected. The corneal reflection light also becomes incident on the detecting element 57, so that the deformed state of the cornea Ec can similarly be detected based on the output signal from the detecting element 57.

Figure 3:
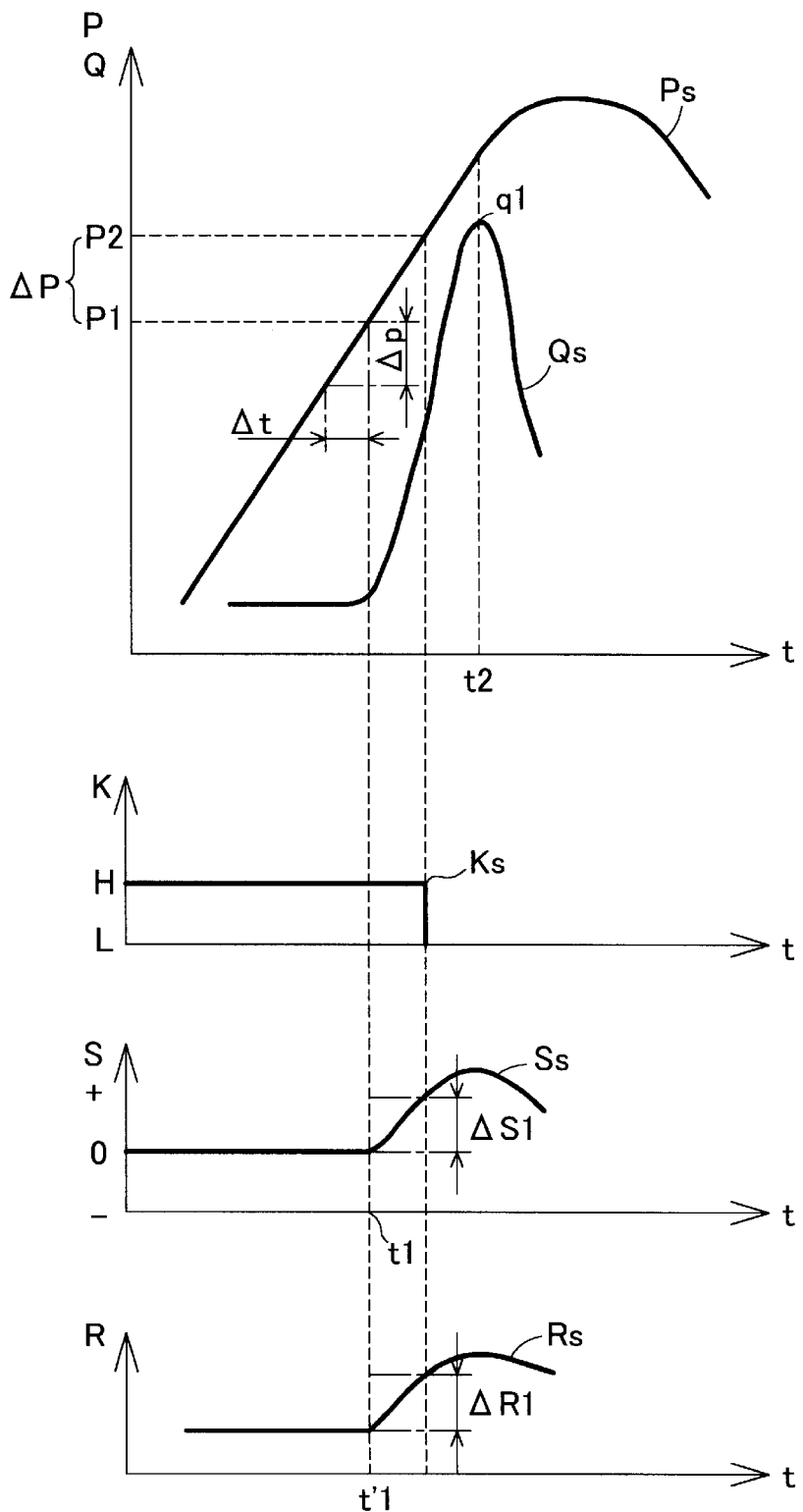
FIG. 3 is a graph showing variations in time series of a pressure signal from a pressure sensor, a corneal deformation signal from a photodetector, a solenoid driving signal, a positional deviation signal and a received light amount signal from a one-dimensional position detecting element.

FIG. 3 is a graph showing, in time series, a pressure signal Ps output from the sensor 12, a corneal deformation signal Qs output from the photodetector 56, a solenoid driving signal Ks, and a positional deviation signal Ss and a received-light amount signal Rs output from the detecting element 57.

When the piston 2 starts to be raised, the air in the compression chamber 11 is compressed, and the pressure signal Ps output from the sensor 12 substantially linearly increases with the rise of the piston 2. The pressure of the compressed air to be blown from the nozzle 6 toward the cornea Ec similarly increases.

The cornea Ec begins to become deformed by the compressed air blown as above. On commencement of deformation of the cornea Ec, the position of the index image detected (or the receiving position of the corneal reflection light received) by the detecting element 57 starts to deviate from the position detected at the alignment completion, or at the measurement start, as in the case that the working distance becomes far. The control circuit 20 obtains a pressure P1 at the deviation start time t1 and stores it in the memory 24. The control circuit 20 continuously or intermittently obtains the pressure in the compression chamber 11 by receiving signals from the sensor 12. When the pressure value P1 is increased by an increment of ΔP into a pressure value P2 (when the index image has deviated by a predetermined amount ΔS1 from the position at the alignment completion or the measurement start), the solenoid driving signal Ks is turned to LOW, thereby stopping the supply of electrical charge to stop the driving of the solenoid 3.

It is to be noted that the piston 2 is raised by an inertial force even after the supply of electric charge to the rotary solenoid 3 is stopped, so that the pressure to be detected by the sensor 12 consecutively increases for a while without decreasing immediately, and then lowers. Accordingly, the increment value ΔP is determined in consideration of the increase in the pressure allowed after stop of driving of the solenoid 3 so that a peak q1 of the corneal deformation signal Qs is obtained.

The increment ΔP may be set to a predetermined value in advance, but it is preferably determined by a function of a change in pressure Δp for a predetermined time Δt, namely, the ratio of pressure change; Δp/Δt, at about the deviation start time t1 (just before the deviation start time t1) of the positional deviation signal Ss. If Δp/Δt is large, which indicates that the inertial force of the piston 2 is large and also the increasing ratio of pressure after the stop of driving of the solenoid 3 is large, the increment ΔP is set to a small value. If Δp/Δt is small, to the contrary, which indicates that the pressure increasing ratio after the stop of driving of the solenoid 3 is small, the increment ΔP is set to a large value.

If the above value, Δp/Δt, is smaller than a fixed value set in advance for any reason, for example, an air leakage from between the cylinder and the piston, the driving of the solenoid 3 is stopped after the corneal deformation signal Qs reaches a peak q1 in order to make sure that the cornea Ec is brought into a predetermined deformed state (an applanation state).

When the cornea Ec begins to become deformed, the amount of the corneal reflection light detected by the detecting element 57 changes from the light amount detected at the alignment completion or the measurement start. With reference to the change start time t'1 of the received-light amount signal Rs instead of the deviation start time t1 of the positional deviation signal Ss, the driving of the solenoid 3 may be stopped at the timing that the detected pressure has changed by ΔP (which is the time when the light amount is increased by a predetermined amount ΔR1 from the amount obtained at the alignment completion or the measurement start).

Although the piston 2 is raised by the inertial force even after the solenoid 3 is stopped, the biasing force caused by the coiled spring in the lowering direction is exerted on the piston 2. The biasing force of the coiled spring and the gravity applied to the piston 2 attenuate the speed of the piston 2. Accordingly, the piston 2 is stopped temporarily and then lowered. The corneal deformation signal Qs is allowed to reach the peak q1 by the pressure increase caused after the stop of the solenoid 3. The control circuit 20 determines an average pressure value Pav(t) of the peak value q1 at about the time t2 and makes a predetermined processing to convert the average value into an intraocular pressure value.

In the above manner, the present apparatus can prevent superfluous air from being blown to the examinee's eye during measurement. As compared with the case that driving of the solenoid 3 is stopped after detection that the cornea Ec has been deformed into a predetermined state, the present apparatus enables measurement with a lower blowing pressure from the first intraocular measurement.

Figure 4:
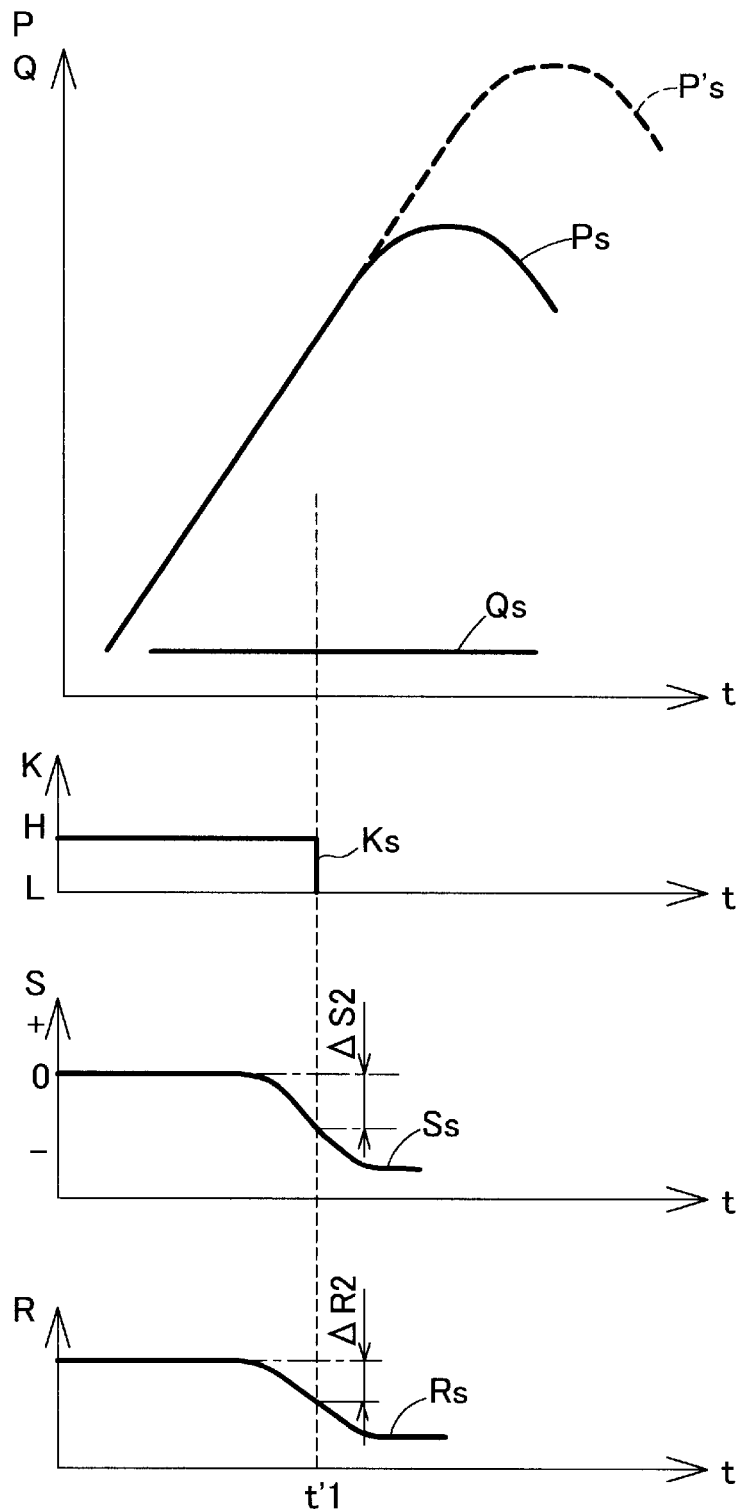
FIG. 4 is a graph showing variations in time series of a pressure signal, a corneal deformation signal, a solenoid driving signal, a positional deviation signal and a received light amount signal, in a case where a blink of an examinee's eye occurs.

Next, another case where an eye blink occurs after start of measurement is described with reference to FIG. 4.

The occurrence of the blink of the eye E prevents the corneal reflection light from becoming incident on the photodetector 56, which brings about little or no change in the corneal deformation signal Qs, producing no peak. Due to no peak in the signal Qs, in the structure that the driving of the solenoid 3 is stopped only after the corneal deformation signal Qs reaches a peak, the compressed air is blown up to the predetermined maximum pressure as shown by the pressure signal P's in FIG. 4.

If the blink occurs after start of measurement on completion of the alignment, on the other hand, the received-light amount signal Rs from the detecting element 57 largely decreases. The positional deviation signal Ss representative of the detected working distance also widely changes in the direction indicating that the working distance becomes shorter. When the control circuit 20 detects that the positional deviation signal Ss has changed in the direction that the working distance became shorter by ΔS2 or detects that the received-light amount signal Rs has decreased by ΔR2, it stops the driving of the solenoid 3. The above ΔS2 and ΔR2 are determined as the values enough to surely detect a blink. The above manner can interrupt measurement without blowing superfluous air to the examinee's eye at the occurrence of a blink. In this case, the control circuit 20 causes the monitor 36 to display to that effect that a measurement error occurs.

In the above embodiment, the solenoid is used as a driving source of the piston. Other driving sources may be used. For example, a motor may be used. Alternatively, a pump, a solenoid valve, or the like may be used to pneumatically drive the piston.

As described above, according to the present invention, measurement can be effected without blowing unnecessary air to the examinee's eye. Blowing of superfluous air can also be prevented at the occurrence of a blink. Thus, a burden to the examinee's eye can be reduced and thus measurement results with high accuracy can be obtained.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A non-contact type tonometer including:
    a compressed air blowing unit which compresses air in a cylinder by means of a piston disposed within the cylinder and blows the compressed air to a cornea of an examinee's eye;
    a driving unit which drives the piston;
    a pressure sensor which detects pressure of the air in the cylinder;
    an optical system which projects light to the cornea;
    a photosensor which detects, of the light projected by the optical system, reflection light reflected from the cornea; and
    a controller which obtains a change in pressure for a predetermined time based on a detection result by the pressure sensor when the photosensor detects a predetermined change amount of the reflection light after the driving unit drives the piston to start blowing of the compressed air to the cornea from the compressed air blowing unit, and changes a timing of stopping supply of driving power to the driving unit based on the obtained change in pressure.

2. The non-contact type tonometer according to claim 1, wherein the photosensor detects at least one of a deviation amount of a positional deviation signal and a change amount of a received light amount signal.

3. The non-contact type tonometer according to claim 2, wherein the controller stops the supply of driving power to the driving unit when a difference between a pressure value detected at the time when the positional deviation signal or the received light amount signal starts to deviate or change and another pressure value detected at the time when the positional deviation signal or the received light amount signal has changed by a predetermined deviation amount or a predetermined change amount becomes equal to a predetermined change amount in pressure.

4. A non-contact type tonometer including:
    a compressed air blowing unit which compresses air in a cylinder by means of a piston disposed within the cylinder and blows the compressed air to a cornea of an examinee's eye;
    a driving unit which drives the piston;
    a pressure sensor which detects pressure of the air in the cylinder;
    an optical system which projects light to the cornea;
    a one-dimensional position detecting element which detects reflection light corresponding to a working distance to the cornea based on the light projected by the optical system and then reflected from the cornea; and
    a controller which obtains a change in pressure for a predetermined time based on a detection result by the pressure sensor when the one-dimensional position detecting element detects a predetermined change amount of the reflection light after the driving unit drives the piston to start blowing of the compressed air to the cornea from the compressed air blowing unit, and changes a timing of stopping supply of driving power to the driving unit based on the obtained change in pressure.

5. The non-contact type tonometer according to claim 4, wherein the one-dimensional position detecting element detects at least one of a deviation amount of a positional deviation signal and a change amount of a received light amount signal.

6. The non-contact type tonometer according to claim 5, wherein the controller stops the supply of driving power to the driving unit when a difference between a pressure value detected at the time when the positional deviation signal or the received light amount signal starts to deviate or change and another pressure value detected at the time when the positional deviation signal or the received light amount signal has changed by a predetermined deviation amount or a predetermined change amount becomes equal to a predetermined change amount in pressure.

7. A non-contact type tonometer including:
    a compressed air blowing unit which compresses air in a cylinder by means of a piston disposed within the cylinder and blows the compressed air to a cornea of an examinee's eye;
    a driving unit which drives the piston;
    a pressure sensor which detects pressure of the air in the cylinder;
    an optical system which projects light to the cornea;

a photosensor which detects, of the light projected by the optical system, reflection light reflected from the cornea; and a controller which obtains a pressure change ratio expressed in a pressure change amount with respect to a predetermined time just before a predetermined change amount of the reflection light is detected by the photosensor after the driving unit drives the piston to start blowing of the compressed air to the cornea from the compressed air blowing unit, and sets the pressure change amount to a small value when the obtained pressure change ratio is large and, alternatively, to a large value when the obtained pressure change ratio is small, and stops supply of driving power to the driving unit based on the set pressure change amount.

8. The non-contact type tonometer according to claim 7, wherein the photosensor includes a one-dimensional position detecting element which detects the reflection light corresponding to a working distance to the cornea based on the light projected by the optical system and then reflected from the cornea.

9. The non-contact type tonometer according to claim 7, wherein the photosensor detects at least one of a deviation amount of a positional deviation signal and a change amount of a received light amount signal.

10. A non-contact type tonometer including:

a compressed air blowing unit which compresses air in a cylinder by means of a piston disposed within the cylinder and blows the compressed air to a cornea of an examinee's eye;

a driving unit which drives the piston;

an optical system which projects light to the cornea;

a photosensor which detects, of the light projected by the optical system, reflection light reflected from the cornea; and a controller which judges that a blink of the examinee's eye has occurred when a change amount of the reflection light detected by the photosensor decreases by a predetermined amount after the driving unit drives the piston to start blowing of the compressed air to the cornea from the compressed air blowing unit, and stops supply of driving power to the driving unit.

11. The non-contact type tonometer according to claim 10, wherein the photosensor includes a one-dimensional position detecting element which detects the reflection light corresponding to a working distance to the cornea based on the light projected by the optical system and then reflected from the cornea.

12. The non-contact type tonometer according to claim 10, wherein the photosensor detects at least one of a deviation amount of a positional deviation signal and a change amount of a received light amount signal.

* * * * *